(12) United States Patent
Dai et al.

(10) Patent No.: US 12,345,694 B2
(45) Date of Patent: Jul. 1, 2025

(54) AUTOMATIC WATERMELON INSPECTION APPARATUS

(71) Applicant: Sihui Dai, Hunan (CN)

(72) Inventors: Sihui Dai, Hunan (CN); Jingjing Huang, Hunan (CN); Ming Li, Hunan (CN); Ting Zou, Hunan (CN); Yongwei Xu, Guangdong (CN); Heming Hu, Hunan (CN); Hongduo Zhang, Hunan (CN); Zhiwei Wang, Hunan (CN); Liang Zhang, Hunan (CN); Jinqi Huang, Hunan (CN); Hao Xiong, Hunan (CN); Yunong Zhou, Hunan (CN); Wenting Zhou, Hunan (CN); Siping Yu, Hunan (CN); XiongWei Gong, Hunan (CN)

(73) Assignee: Sihui Dai, Changsha (CN)

( * ) Notice: Subject to any disclaimer, the term of this patent is extended or adjusted under 35 U.S.C. 154(b) by 340 days.

(21) Appl. No.: 18/168,353

(22) Filed: Feb. 13, 2023

(65) Prior Publication Data
US 2023/0304986 A1 Sep. 28, 2023

(30) Foreign Application Priority Data

Mar. 22, 2022 (CN) .......................... 202210285855.8
Sep. 12, 2022 (JP) ................................ 2022-144489

(51) Int. Cl.
*A23N 1/02* (2006.01)
*G01N 33/02* (2006.01)

(52) U.S. Cl.
CPC ............. *G01N 33/025* (2013.01); *A23N 1/02* (2013.01)

(58) Field of Classification Search
CPC .......... G01N 33/025; A23N 1/02; B26D 3/30; B02C 4/08; B02C 23/08; B08B 3/02
See application file for complete search history.

(56) References Cited

U.S. PATENT DOCUMENTS 7,600,642 B2 * 10/2009 Deppermann ......... G01N 35/02
 209/552
2010/0143558 A1 * 6/2010 Aharonovitch .......... A23N 1/02
 426/489

(Continued)

FOREIGN PATENT DOCUMENTS

JP H09-101273 A 4/1997

*Primary Examiner* — David J Bolduc
(74) *Attorney, Agent, or Firm* — PV IP PC; Wei Te Chung; Christopher S. Ruprecht

(57) ABSTRACT

An automatic watermelon inspection apparatus includes a weighing and fixing unit, a suction unit, an adjustable cutting unit, an imaging unit, a sugar content measuring unit, a lateral pushing unit, a crushing and pressing unit, a seed separating unit, and a frame. The suction unit sucks a watermelon and raises or releases the watermelon, the weighing and fixing unit includes a movable workbench, a weighing sensor, and a groove, the adjustable cutting unit cuts the watermelon located at a cutting position in a horizontal direction, the sugar content measuring unit is provided above the weighing and fixing unit, the imaging unit acquires information on an outline image and information on a cross-sectional image of the watermelon, the lateral pushing unit pushes the watermelon to the crushing and pressing unit, and the crushing and pressing unit crushes and presses the watermelon in a manner of forming a gap.

7 Claims, 6 Drawing Sheets

(56) References Cited

U.S. PATENT DOCUMENTS

2011/0232507 A1* 9/2011 Aharonovitch .......... A23N 1/02
99/501
2015/0374025 A1* 12/2015 Evans ...................... A23N 1/02
99/495

* cited by examiner

AUTOMATIC WATERMELON INSPECTION APPARATUS

TECHNICAL FIELD

The present invention relates to an automatic watermelon inspection apparatus.

BACKGROUND ART

The watermelon is a therophyte trailing plant belonging to the Cucurbitaceae family, *Citrullus*, is known as "the king of summer fruit" and is an important economic crop in the world. China is the largest watermelon production and consumption country in the world, and is also a major watermelon breeding country, and inspection of the watermelon is very important in a breeding process. Regarding the inspection of the watermelon, it is necessary to collect phenotypes and quality information of the watermelon based on weighing, outline, analysis of a cross-sectional image, sugar content measurement of pulp, or the like, and separate watermelon seeds from pulp to finally facilitate collection of the watermelon seeds.

JPH09-101273A describes a method for non-destructively inspecting internal quality of a watermelon.

SUMMARY OF INVENTION

However, since the method described in JPH09-101273A is a non-destructive inspection method, cross section analysis of the watermelon and precise analysis on the watermelon seeds cannot be performed.

In addition, since a general destructive inspection method mainly depends on a manual operation, there is a problem that not only a breeding cost is required, but also an operation reference for the manual operation is difficult to be unified.

Therefore, in view of such circumstances, an object of the present invention is to provide an automatic watermelon inspection apparatus capable of improving watermelon breeding efficiency by lowering a cost and reducing an operation variation in a watermelon breeding process.

According to one aspect of the present invention, an automatic watermelon inspection apparatus is provided. The automatic watermelon inspection apparatus includes:
  a weighing and fixing unit;
  a suction unit;
  an adjustable cutting unit;
  an imaging unit;
  a sugar content measuring unit;
  a lateral pushing unit;
  a crushing and pressing unit;
  a seed separating unit; and
  a frame, in which
  the suction unit is provided on the frame, sucks a watermelon, and raises or releases the watermelon,
  the weighing and fixing unit is provided below the suction unit, and includes a movable workbench switchable between a measuring position and a cutting position, a weighing sensor, and a V-shaped fixing groove for preventing rolling of the watermelon in a front-rear direction,
  the adjustable cutting unit is provided on one side of the weighing and fixing unit, and cuts the watermelon located at the cutting position in a horizontal direction,
  the sugar content measuring unit is provided above the weighing and fixing unit,
  the imaging unit acquires information on an outline image and information on a cross-sectional image of the watermelon, and acquires, by a mounted computer, an outline shape, a cross-sectional shape, a size, a thickness of watermelon rind, and a shape distortion coefficient parameter of the watermelon,
  the lateral pushing unit pushes the watermelon located in the V-shaped fixing groove to the crushing and pressing unit, a position of the lateral pushing unit corresponding to the V-shaped fixing groove when the movable workbench moves to the cutting position,
  the crushing and pressing unit presses and crushes the watermelon in a manner of forming a gap, and
  the seed separating unit separates a watermelon seed, watermelon juice, and watermelon rind from a residue of the watermelon after pressed and crushed by the crushing and pressing unit, and collects the watermelon seed.

It is preferable that the automatic watermelon inspection apparatus further includes:
  a moving cylinder provided on the movable workbench and having an extendable and contractible piston rod;
  a guide rail provided on the frame;
  a first slider provided on the movable workbench and configured to slide along the guide rail; and
  a stopper provided on the frame and connected to a tip end of the piston rod of the moving cylinder such that the movable workbench switches between the measuring position and the cutting position.

It is preferable that the suction unit includes an upright cylinder vertically provided on the frame, and an adsorption disk provided at a tip end of a piston rod of the upright cylinder, and the upright cylinder is attached directly above the V-shaped fixing groove when the movable workbench moves to the cutting position.

It is preferable that the adjustable cutting unit includes a cutter, a cutter holder, a cutter height adjustment slider module, a cutter holder seat, and a cut cylinder,
  the cutter is fixed to the cutter holder, and the cutter holder is connected to the cutter holder seat via the cutter height adjustment slider module to achieve different cut heights,
  the cutter holder seat and the movable workbench where the weighing and fixing unit is located move along the guide rail, and
  the cut cylinder cuts the watermelon located at the cutting position in the horizontal direction by pushing the cutter, a distance between a cut cross section and the imaging unit is determined in advance, and image analysis of the cross section is performed.

It is preferable that a second slider engaged with the guide rail is provided at a bottom portion of the cutter holder seat.

It is preferable that the crushing and pressing unit includes a first pressing roller, a second pressing roller, a second crushing roller, an adjusting bolt, a first crushing roller, a liner plate, and a motor,
  an output shaft of the motor is connected to the first pressing roller,
  the first pressing roller and the second pressing roller are provided parallel to each other and move in opposite directions to crush and press the watermelon in a manner of forming a gap,
  the first pressing roller and the second pressing roller are synchronized with movements of the first crushing roller and the second crushing roller, respectively,
  the adjusting bolt adjusts an operation gap between the first crushing roller and the second crushing roller, and an operation gap between the first pressing roller and the second pressing roller, and the liner plate is in close contact with the rollers.

It is preferable that the seed separating unit includes a strainer on which the residue of the watermelon after pressing is to be placed, a high-pressure injection gun that separates the watermelon seed, the watermelon juice, and the watermelon rind by cleaning the residue of the watermelon, and a seed outlet provided with a filter that receives the cleaned watermelon seed, the watermelon juice, and water, and collects the watermelon seed.

According to the aspect of the present invention, it is possible to improve watermelon breeding efficiency by lowering a cost and reducing an operation variation in a watermelon breeding process.

DESCRIPTION OF EMBODIMENTS

Hereinafter, an embodiment for carrying out the present invention (hereinafter simply referred to as the embodiment) will be described in detail.

Figure 1:
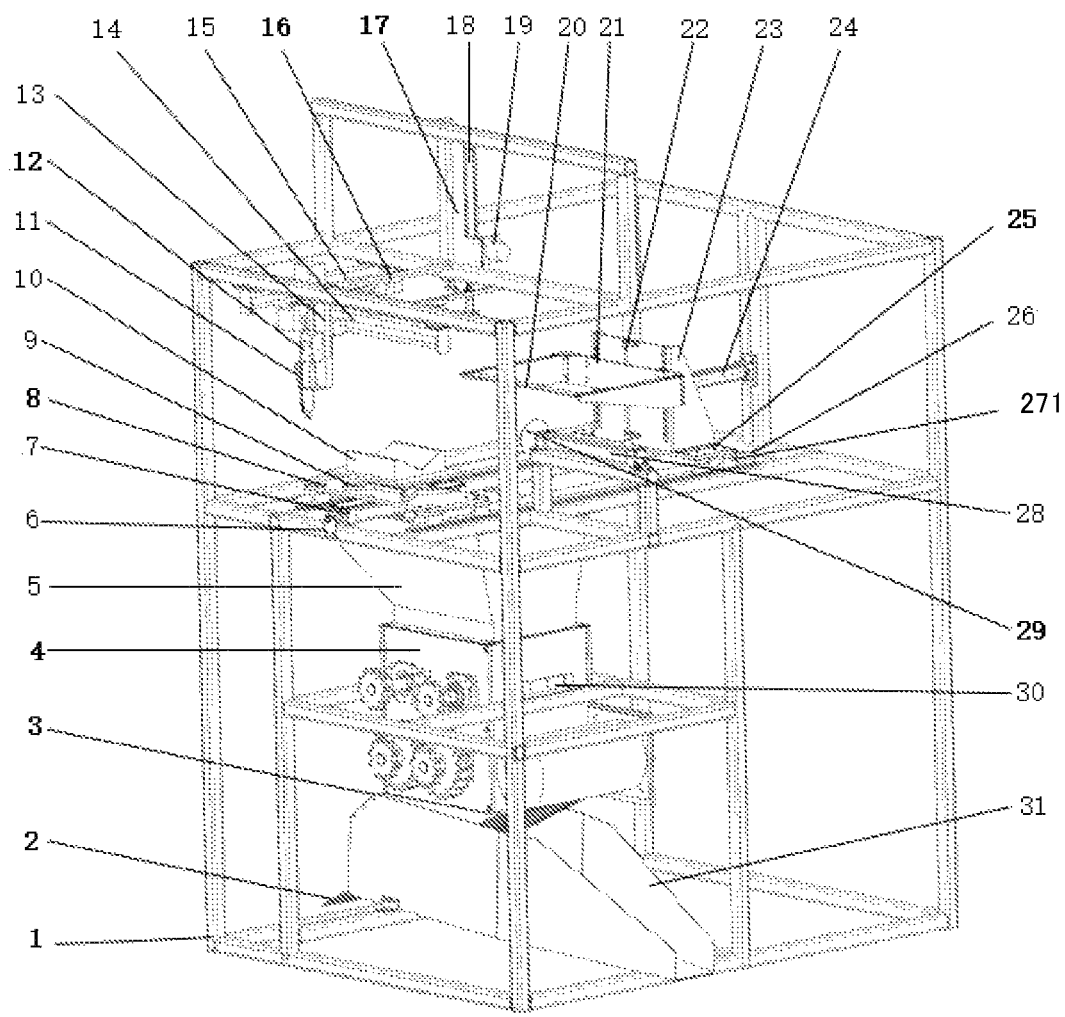
FIG. 1 is a perspective view of an embodiment of the present invention.
Figure 1:
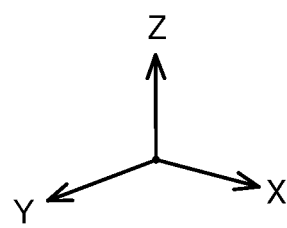
Figure 2:
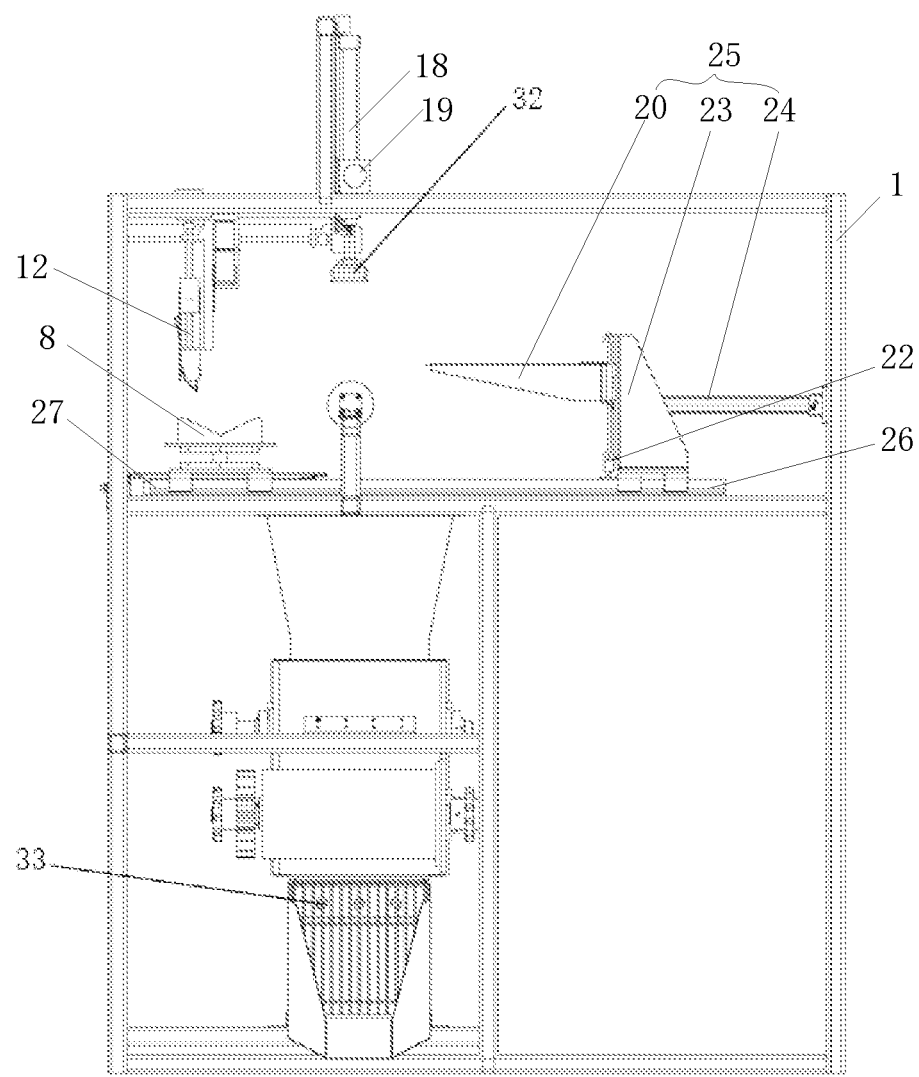
FIG. 2 is a front view of the embodiment of the present invention.
Figure 3:
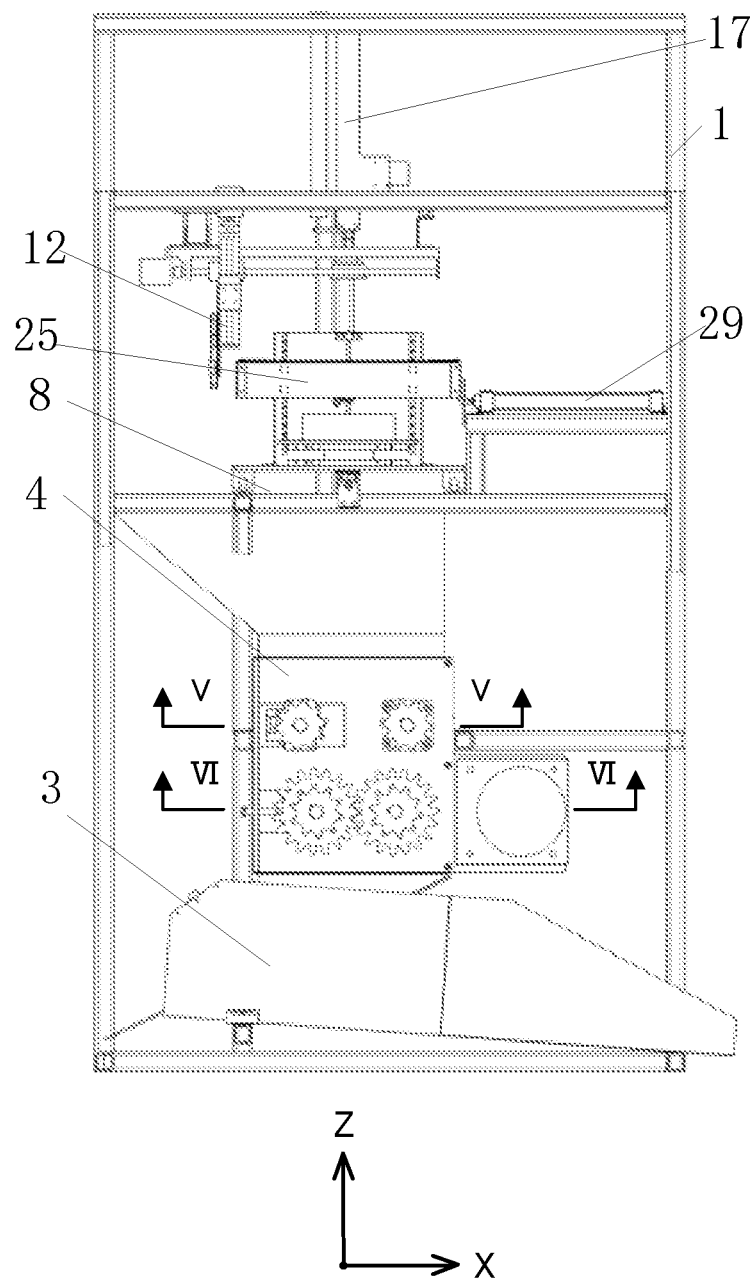
FIG. 3 is a left side view of the embodiment of the present invention.
Figure 4:
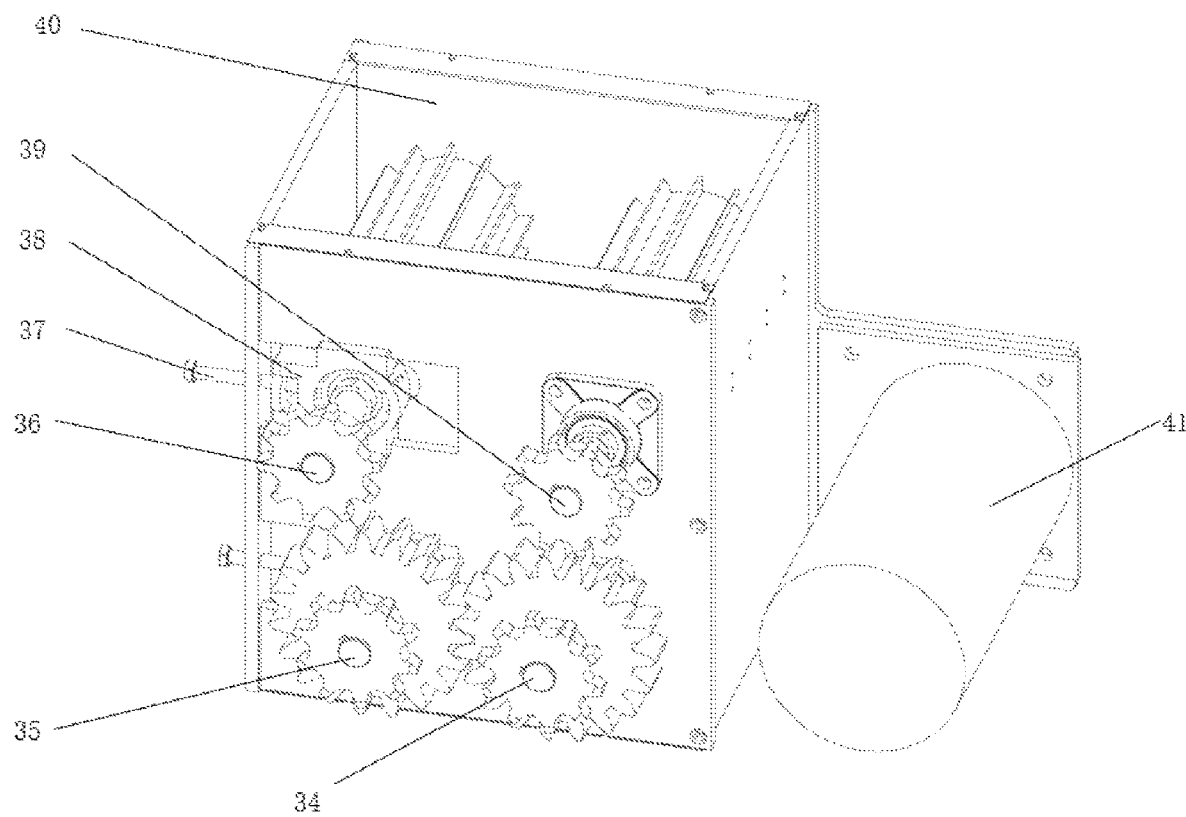
FIG. 4 is a perspective view of a crushing and pressing unit according to the embodiment of the present invention.
Figure 5:
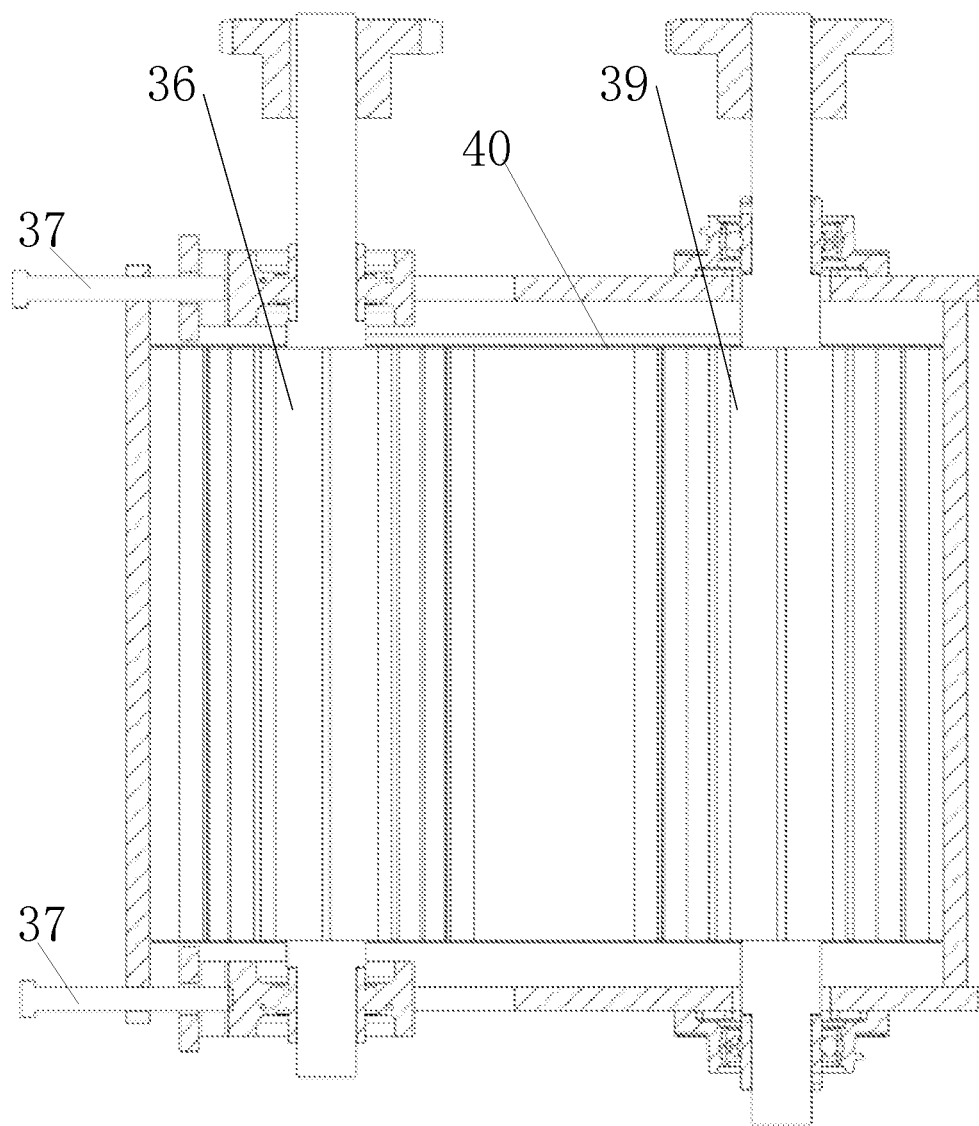
FIG. 5 is a cross-sectional view taken along a line V-V of the FIG. 3.
Figure 6:
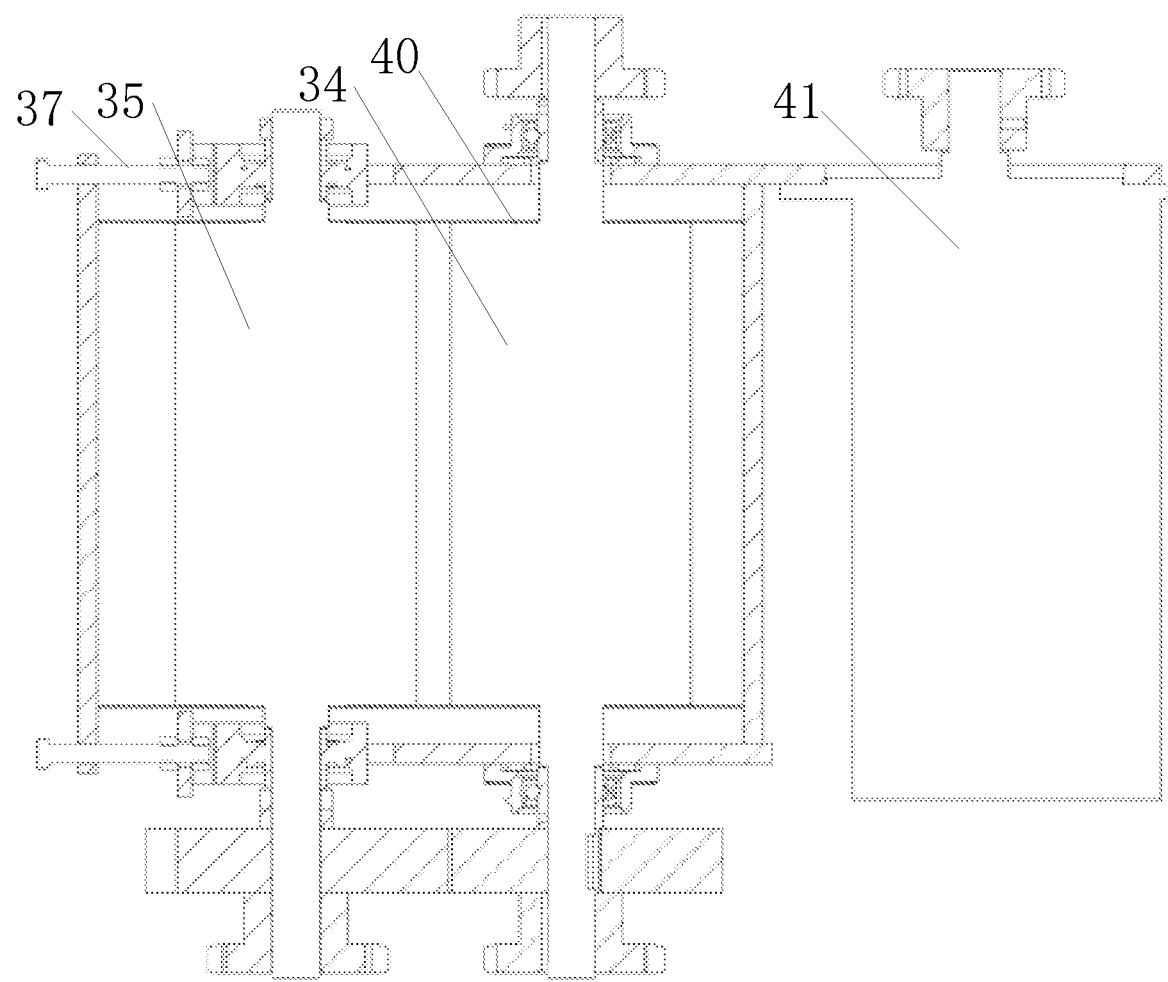
FIG. 6 is a cross-sectional view taken along a line VI-VI of the FIG. 3.

As illustrated in FIGS. 1 to 6, according to the present embodiment, there is provided an automatic watermelon inspection apparatus that includes a weighing and fixing unit 8, a suction unit 17, an adjustable cutting unit 25, an imaging unit 16, a sugar content measuring unit 12, a lateral pushing unit 29, a crushing and pressing unit 4, a seed separating unit 3, a frame 1, and a computer serving as a control unit.

The weighing and fixing unit 8 includes a movable workbench, a weighing sensor 9, and a V-shaped fixing groove 10. The movable workbench is provided with a first slider 27. The frame 1 is provided with a guide rail 26 that extends along a first horizontal direction (left-right direction/Y-axis direction in FIG. 2) and that engages with the first slider 27. When the first slider 27 slides along the guide rail 26, the movable workbench moves along the first horizontal direction. The automatic watermelon inspection apparatus further includes a moving cylinder 7 for switching the movable workbench between a measuring position and a cutting position, and a stopper 6 provided on the frame 1. The moving cylinder 7 has an extendable and contractible piston rod that is provided on the movable workbench. Specifically, the moving cylinder 7 is provided such that the extendable and contractible piston rod extends along the first horizontal direction. The stopper 6 is connected to a tip end of the piston rod of the moving cylinder 7 such that the movable workbench switches between the measuring position and the cutting position. The V-shaped fixing groove 10 can prevent rolling of a watermelon in a front-rear direction, improve a stress distribution at the time of adsorption, more appropriately fix the watermelon, and at the same time reduce damage to the watermelon.

The suction unit 17 includes an upright cylinder 18 having a piston rod movable along a vertical direction, and an adsorption disk 32 provided at a tip end (lower end in FIG. 2) of the piston rod. The upright cylinder 18 is attached to the frame 1 in a manner of being located directly above the V-shaped fixing groove 10 when the movable workbench moves to the cutting position. The adsorption disk 32 is driven by a negative pressure, thereby achieving adsorption, raising, and releasing of the watermelon.

The adjustable cutting unit 25 includes a rope length measuring sensor 19, a cutter 20, a cutter holder 21, a cutter height adjustment slider module 22, a cutter holder seat 23, and a cut cylinder 24. The rope length measuring sensor 19 is attached to one side of the upright cylinder 18 in parallel, and a measurement rope for measuring an expansion and contraction amount of the piston rod of the upright cylinder 18 is fixed to the tip end of the piston rod of the upright cylinder 18. Further, the rope length measuring sensor 19 measures the expansion and contraction amount of the piston rod of the upright cylinder 18 when the adsorption disk 32 is in contact with a top portion of the watermelon, and outputs the expansion and contraction amount to the computer. The computer can calculate a diameter of the watermelon based on the measured expansion and contraction amount of the piston rod of the upright cylinder 18. Then, the computer calculates a cut height of the cutter 20 corresponding to the diameter of the watermelon based on the calculated diameter of the watermelon, and outputs the cut height to the cutter height adjustment slider module 22. The cutter 20 is fixed to the cutter holder 21, and the cutter holder 21 is connected to the cutter holder seat 23 via the cutter height adjustment slider module 22 to achieve different cut heights. A second slider 271 engaged with the guide rail 26 is provided at a bottom portion of the cutter holder seat 23. The cutter holder seat 23 is connected to the frame 1 via the second slider 271 and the guide rail 26, and thus can move along the guide rail 26 together with the movable workbench where the weighing and fixing unit 8 is located. The cut cylinder 24 is provided on the frame 1 such that a piston rod of the cut cylinder 24 extends along the first horizontal direction. A tip end of the piston rod of the cut cylinder 24 is connected to the cutter holder seat 23. The cut cylinder 24 cuts the watermelon located at the cutting position in the horizontal direction by pushing the cutter 20 via the cutter holder seat 23. Since a distance between a cut cross section and the imaging unit 16 is determined in advance, image analysis of the cross section of the watermelon is performed by the computer.

The imaging unit 16 is attached to the frame 1 in a manner of being located above the movable workbench. Regarding a half of the watermelon placed in the V-shaped fixing groove 10, the imaging unit 16 acquires information on an outline image and information on a cross-sectional image of the watermelon, acquires, by the mounted computer, an outline shape, a cross-sectional shape, a size, a thickness of watermelon rind, and a shape distortion coefficient parameter of the watermelon, and acquires coordinate values of measured points at a center of the cross section and an edge portion of the watermelon by the image analysis.

The sugar content measuring unit 12 includes a sugar content sensor 11, a Z-axis slider module 13 that raises and lowers the sugar content sensor 11 along the vertical direction (up-down direction/Z-axis direction in FIG. 1), an X-axis slider module 14 that moves the Z-axis slider module 13 along a second horizontal direction (left-right direction/X-axis direction in FIG. 3) orthogonal to the first horizontal direction, and a Y-axis slider module 15 that moves the X-axis slider module 14 along the first horizontal direction.

The sugar content sensor 11 may be inserted into pulp to come into contact with juice and measure a sugar content, or may be replaced with a contactless measuring sensor to achieve the same function. The Z-axis slider module 13 includes a vertical guide pole provided in a manner of extending along the vertical direction, and an elevating slider connected to the sugar content sensor 11 in a manner of sliding along the vertical guide pole. The X-axis slider module 14 includes a first horizontal guide pole provided in a manner of extending along the first horizontal direction, and a first horizontal slider connected to the Z-axis slider module 13 in a manner of sliding along the first horizontal guide pole. The Y-axis slider module 15 includes a second horizontal guide pole provided in a manner of extending along the second horizontal direction, and a second horizontal slider connected to the X-axis slider module 14 in a manner of sliding along the second horizontal guide pole. A triaxial robot arm function for moving the sugar content sensor 11 to a designated measuring position can be achieved by using the X-axis slider module 14, the Y-axis slider module 15, and the Z-axis slider module 13.

The lateral pushing unit 29 pushes the watermelon located in the V-shaped fixing groove 10 to a feed hopper 5, and is provided on the frame 1 such that a position of the lateral pushing unit 29 corresponds to the V-shaped fixing groove 10 when the movable workbench where the weighing and fixing unit 8 is located moves to the cutting position. Specifically, the lateral pushing unit 29 is implemented by an extendable and contractible cylinder having a piston rod along a second direction. By extending the piston rod, a tip end of the piston rod can push the cut watermelon to fall into the feed hopper 5.

The crushing and pressing unit 4 includes a first pressing roller 34, a second pressing roller 35, a second crushing roller 36, an adjusting bolt 37, a UCP bearing 38, a first crushing roller 39, a liner plate 40, and a motor 41. A sprocket is used between an output shaft of the motor 41 and the first pressing roller 34, and thus power of the motor 41 is transmitted to the first pressing roller 34. Since gear transmission occurs between the first pressing roller 34 and the second pressing roller 35, movements in opposite directions of the two rollers can be achieved. Accordingly, the watermelon is pressed in a manner that a gap is formed. Sprocket transmission is adopted between the first pressing roller 34 and the first crushing roller 39, and between the second pressing roller 35 and the second crushing roller 36, and maintaining movements of the two crushing rollers and the two pressing rollers in synchronization with each other can be achieved. Further, by crushing the watermelon cut in half using tooth pieces circumferentially distributed uniformly on the crushing rollers and conveying the watermelon downward, it is possible to avoid a problem that a pressing operation is difficult to be performed normally since a surface of the watermelon is too smooth or the strength of the watermelon rind is too high. Each of the second pressing roller 35 and the second crushing roller 36 is fixed to an apparatus body by adopting the UCP bearing 38, and in order to cope with needs for the pressing operation with respect to a wider range of watermelon varieties, an operation gap between the crushing rollers and an operation gap between the pressing rollers may be adjusted by the adjusting bolt 37. In this case, specifically, by screwing or loosening the adjusting bolt 37, the second pressing roller 35 and the second crushing roller 36 can be brought close to or separated from the first pressing roller 34 and the first crushing roller 39, respectively. The liner plate 40 is in close contact with the rollers, and by adopting a clearance fit, broken pieces, seeds and the like of the watermelon at the time of the crushing and the pressing operation are less likely to enter, and thus it is convenient for cleaning, and it is possible to properly avoid mixing of the seeds.

The seed separating unit 3 includes a strainer 2 on which a residue of the watermelon after pressing is to be placed, a high-pressure injection gun 33 that separates the watermelon seeds, the watermelon juice, and the watermelon rind by cleaning the residue of the watermelon, and a seed outlet 31 provided with a filter that receives the cleaned watermelon seeds, the watermelon juice, and water, and collects the watermelon seeds.

An operation process of the embodiment according to the present invention is as follows. A user places a watermelon in the V-shaped fixing groove 10 such that a major axis of the watermelon is parallel to the second direction, acquires a weight of the watermelon measured by the weighing sensor 9, and acquires information on an outline image of the watermelon by the imaging unit 16. The watermelon is driven to the cutting position by the moving cylinder 7, the adsorption disk 32 is driven to press the watermelon downward by the upright cylinder 18, a displacement amount of the adsorption disk is measured by the rope length measuring sensor 19, a height of a central position of the watermelon is estimated based on information on geometric structures of the frame 1, the weighing and fixing unit 8, and the V-shaped fixing groove 10, and a height of the cutter holder 21 of the adjustable cutting unit 25 is controlled, whereby horizontal cutting at an intermediate position can be achieved. The adsorption disk 32 is activated at a negative pressure, and sucks and raises an upper half of the cut watermelon, and a lower half of the watermelon is driven by the moving cylinder 7 to return to the measuring position. The imaging unit 16 acquires image information on a cross section of the watermelon, performs image analysis, analyzes parameters such as a thickness of watermelon rind and a cross-sectional area based on the known distance between the cross section and the imaging unit, and calculates Cartesian coordinate values of measured points for sugar content at a center portion and the edge portion of the watermelon rind. By controlling the X-axis slider module, the Y-axis slider module, and the Z-axis slider module, the sugar content sensor is driven to a measured point designated by the cutter, and is inserted into pulp to be brought into contact with juice, or measures sugar contents in regions in the cross section of the watermelon by non-contact sensing. The upper half of the watermelon is released from the adsorption disk 32, falls into the feed hopper 5 due to gravity and enters the crushing and pressing unit 4. The hemispherical watermelon is crushed by the first crushing roller 39 and the second crushing roller 36 and is fed downward to the first pressing roller 34 and the second pressing roller 35. Since there is a large difference in compression strength between the watermelon seeds and the pulp, the gap between the pressing rollers is always set larger than a maximum envelope diameter of the watermelon, and thus it is possible to ensure that the watermelon seeds are pressed but not damaged while the pulp is pressed to acquire the juice. The residue of the watermelon generated after the pressing is slid down from the strainer 2, the watermelon seeds and the juice are cleaned by the high-pressure injection gun 33 and enter the seed outlet 31, the watermelon seeds are collected by the filtration of the filter, and the residue of the watermelon rind is discharged outside the apparatus. Cleaning of the feed hopper 5 and the crushing and pressing unit 4 is achieved by using a sprinkler head disposed above the feed hopper 5, the structure of the crushing and pressing unit 4 is simple, and thus it is possible to achieve a satisfactory cleaning effect, and it is possible to avoid the problem of mixing of the seeds.

According to the present embodiment, it is possible to improve watermelon breeding efficiency by lowering a cost and reducing an operation variation in a watermelon breeding process.

As described above, the present invention is described in more detail with reference to a specific embodiment, and the specific embodiment of the present invention is not considered to be limited to the description. For those skilled in the art, many embodiments can be obtained by the simple deduction or alternation without departing the spirit of the present invention.

The present application claims priorities of Chinese Patent Application No. 202210285855.8 filed to the China Patent Office on Mar. 22, 2022, and Japanese Patent Application No. 2022-144489 filed to the Japan Patent Office on Sep. 12, 2022, all the contents of which are hereby incorporated by reference.

The invention claimed is:

1. An automatic watermelon inspection apparatus comprising:
   a weighing and fixing unit;
   a suction unit;
   an adjustable cutting unit;
   an imaging unit;
   a sugar content measuring unit;
   a lateral pushing unit;
   a crushing and pressing unit;
   a seed separating unit; and
   a frame, wherein
   the suction unit is provided on the frame, sucks a watermelon, and raises or releases the watermelon,
   the weighing and fixing unit is provided below the suction unit, and includes a movable workbench switchable between a measuring position and a cutting position, a weighing sensor, and a V-shaped fixing groove for preventing rolling of the watermelon in a front-rear direction,
   the adjustable cutting unit is provided on one side of the weighing and fixing unit, and cuts the watermelon located at the cutting position in a horizontal direction,
   the sugar content measuring unit is provided above the weighing and fixing unit,
   the imaging unit acquires information on an outline image and information on a cross-sectional image of the watermelon, and acquires, by a mounted computer, an outline shape, a cross-sectional shape, a size, a thickness of watermelon rind, and a shape distortion coefficient parameter of the watermelon,
   the lateral pushing unit pushes the watermelon located in the V-shaped fixing groove to the crushing and pressing unit, a position of the lateral pushing unit corresponding to the V-shaped fixing groove when the movable workbench moves to the cutting position,
   the crushing and pressing unit presses and crushes the watermelon in a manner of forming a gap, and
   the seed separating unit separates a watermelon seed, watermelon juice, and watermelon rind from a residue of the watermelon after pressed and crushed by the crushing and pressing unit, and collects the watermelon seed.

2. The automatic watermelon inspection apparatus according to claim 1, further comprising:
   a moving cylinder provided on the movable workbench and having an extendable and contractible piston rod;
   a guide rail provided on the frame;
   a first slider provided on the movable workbench and configured to slide along the guide rail; and
   a stopper provided on the frame and connected to a tip end of the piston rod of the moving cylinder such that the movable workbench switches between the measuring position and the cutting position.

3. The automatic watermelon inspection apparatus according to claim 2, wherein
   the suction unit includes an upright cylinder vertically provided on the frame, and an adsorption disk provided at a tip end of a piston rod of the upright cylinder, and
   the upright cylinder is attached directly above the V-shaped fixing groove when the movable workbench moves to the cutting position.

4. The automatic watermelon inspection apparatus according to claim 3, wherein
   the adjustable cutting unit includes a cutter, a cutter holder, a cutter height adjustment slider module, a cutter holder seat, and a cut cylinder,
   the cutter is fixed to the cutter holder, and the cutter holder is connected to the cutter holder seat via the cutter height adjustment slider module to achieve different cut heights,
   the cutter holder seat and the movable workbench where the weighing and fixing unit is located move along the guide rail, and
   the cut cylinder cuts the watermelon located at the cutting position in the horizontal direction by pushing the cutter, a distance between a cut cross section and the imaging unit is determined in advance, and image analysis of the cross section is performed.

5. The automatic watermelon inspection apparatus according to claim 4, wherein
   a second slider engaged with the guide rail is provided at a bottom portion of the cutter holder seat.

6. The automatic watermelon inspection apparatus according to claim 1, wherein
   the crushing and pressing unit includes a first pressing roller, a second pressing roller, a second crushing roller, an adjusting bolt, a first crushing roller, a liner plate, and a motor,
   an output shaft of the motor is connected to the first pressing roller,
   the first pressing roller and the second pressing roller are provided parallel to each other and move in opposite directions to crush and press the watermelon in a manner of forming a gap,
   the first pressing roller and the second pressing roller are synchronized with movements of the first crushing roller and the second crushing roller, respectively,
   the adjusting bolt adjusts an operation gap between the first crushing roller and the second crushing roller, and an operation gap between the first pressing roller and the second pressing roller, and
   the liner plate is in close contact with the rollers.

7. The automatic watermelon inspection apparatus according to claim 1, wherein
   the seed separating unit includes a strainer on which the residue of the watermelon after pressing is to be placed, a high-pressure injection gun that separates the watermelon seed, the watermelon juice, and the watermelon rind by cleaning the residue of the watermelon, and a seed outlet provided with a filter that receives the cleaned watermelon seed, the watermelon juice, and water, and collects the watermelon seed.

* * * * *